(12) United States Patent
Ukon et al.

(10) Patent No.: US 9,116,116 B2
(45) Date of Patent: Aug. 25, 2015

(54) OPTICAL ANALYZER AND WAVELENGTH STABILIZED LASER DEVICE FOR ANALYZER

(75) Inventors: Juichiro Ukon, Kyoto (JP); Takuya Ido, Kyoto (JP); Susumu Mimura, Kyoto (JP)

(73) Assignee: HORIBA, LTD., Kyoto (JP)

( * ) Notice: Subject to any disclaimer, the term of this patent is extended or adjusted under 35 U.S.C. 154(b) by 1145 days.

(21) Appl. No.: 12/935,155

(22) PCT Filed: Mar. 27, 2009

(86) PCT No.: PCT/JP2009/056234
§ 371 (c)(1),
(2), (4) Date: Sep. 28, 2010

(87) PCT Pub. No.: WO2009/119790
PCT Pub. Date: Oct. 1, 2009

(65) Prior Publication Data
US 2011/0019183 A1  Jan. 27, 2011

(30) Foreign Application Priority Data

Mar. 28, 2008 (JP) .................................. 2008-087065
Apr. 25, 2008 (JP) .................................. 2008-116239

(51) Int. Cl.
*H01S 5/024* (2006.01)
*H01S 5/068* (2006.01)
(Continued)

(52) U.S. Cl.
CPC .................. *G01N 21/39* (2013.01); *G01J 3/108* (2013.01); *G01N 21/3504* (2013.01);
(Continued)

(58) Field of Classification Search
CPC ............ H01S 5/02248; H01S 5/02415; H01S 5/06213; H01S 5/0687; H01S 5/024
USPC ........................ 372/38.01, 29.011, 29.015, 32
See application file for complete search history.

(56) References Cited

U.S. PATENT DOCUMENTS

| 5,025,448 A | 6/1991 | Sudo et al. |
| 5,202,570 A | 4/1993 | Tanaka et al. |

(Continued)

FOREIGN PATENT DOCUMENTS

| CN | 1065037 A | 2/2005 |
| CN | 1765037 A | 4/2006 |

(Continued)

*Primary Examiner* — Yuanda Zhang
*Assistant Examiner* — Michael Carter
(74) *Attorney, Agent, or Firm* — Brooks Kushman P.C.

(57) ABSTRACT

Provided is an optical analyzer which can promote enhancement of measurement sensitivity, cost reduction, size reduction, structural flexibility, disturbance resistance, and the like, at the same time. A laser device to be used in such optical analyzer is also provided. An optical analyzer comprises a laser light source (2); a wavelength selection element (3) for selecting and leading out light having a wavelength substantially equal to the absorption wavelength of an analysis object from among light outputted from the laser light source (2); an optical detection means (5) for detecting the intensity of light red out from the wavelength selection element (3); and a drive current control means (6) for increasing or decreasing the drive current of the laser light source (2) near a specified current value thereof for outputting light of the absorption wavelength, and setting the drive current at such a current value as the intensity of light detected by the optical detection means (5) has a peak value. The laser light source (2), the wavelength selection element (3), and the optical detection means (5) are mounted on a single substrate (11) which can regulate the temperature to a constant level.

7 Claims, 12 Drawing Sheets

(51) Int. Cl.
*G01N 21/39* (2006.01)
*G01J 3/10* (2006.01)
*G01N 21/3504* (2014.01)
*G01N 21/77* (2006.01)
*H01S 5/022* (2006.01)
*H01S 5/062* (2006.01)
*H01S 5/0687* (2006.01)

(52) U.S. Cl.
CPC ... *G01N 21/7703* (2013.01); *G01N 2201/0231* (2013.01); *H01S 5/024* (2013.01); *H01S 5/02248* (2013.01); *H01S 5/02415* (2013.01); *H01S 5/0687* (2013.01); *H01S 5/06213* (2013.01)

(56) References Cited

U.S. PATENT DOCUMENTS

| | | | |
|---|---|---|---|
| 5,703,365 | A | 12/1997 | Ishihara et al. |
| 5,867,513 | A | 2/1999 | Sato |
| 7,061,944 | B2* | 6/2006 | DeCusatis et al. ............ 372/18 |
| 7,095,012 | B2* | 8/2006 | Fujisawa et al. .......... 250/269.1 |
| 2001/0022793 | A1* | 9/2001 | Yokoyama ................ 372/29.02 |
| 2003/0039276 | A1 | 2/2003 | Tatsuno et al. ................. 372/31 |
| 2003/0095346 | A1* | 5/2003 | Nasu et al. .................... 359/820 |
| 2003/0109055 | A1 | 6/2003 | Lehmann et al. |
| 2003/0112500 | A1* | 6/2003 | Miki et al. .................... 359/344 |
| 2003/0218750 | A1* | 11/2003 | Friberg et al. ................ 356/437 |
| 2004/0190571 | A1 | 9/2004 | Sutton et al. |
| 2005/0157303 | A1 | 7/2005 | Langford et al. |
| 2006/0159135 | A1* | 7/2006 | Cliche et al. .................... 372/20 |
| 2006/0187976 | A1 | 8/2006 | Mori et al. |

FOREIGN PATENT DOCUMENTS

| | | |
|---|---|---|
| JP | 64-023142 | 1/1989 |
| JP | 05-142146 | 6/1993 |
| JP | 09297061 A | 11/1997 |
| JP | 10-267839 | 10/1998 |
| JP | 2010267839 | 10/1998 |
| JP | 11-326199 | 11/1999 |
| JP | 2011326199 | 11/1999 |
| JP | 2000-035554 A | 2/2000 |
| JP | 2001-21493 | 1/2001 |
| JP | 2001-235418 | 8/2001 |
| JP | 2002-286965 A | 4/2002 |
| JP | 2002-111122 A | 10/2002 |
| JP | 2003-142767 | 5/2003 |
| JP | 2005-061904 | 3/2005 |
| JP | 2005-522694 A | 7/2005 |
| JP | 05522694 | 7/2005 |
| JP | 2005-527838 A | 9/2005 |
| JP | 05527838 | 9/2005 |
| JP | 2006133013 A | 5/2006 |
| JP | 2006522938 A | 10/2006 |
| JP | 2006-352053 | 12/2006 |
| WO | 95/26497 | 10/1995 |

* cited by examiner

OPTICAL ANALYZER AND WAVELENGTH STABILIZED LASER DEVICE FOR ANALYZER

FIELD OF THE ART

This invention relates to an optical analyzer that measures a concentration or a density of an analysis object based on a drop of intensity of light irradiated on the analysis object such as a gas, and a laser device used for the optical analyzer.

BACKGROUND ART

A photo diode for monitoring intensity of laser light is integrally attached to some laser light source represented by a semiconductor laser. In accordance with this laser light source, since it is possible to dynamically control a driving electric current with monitoring an output signal from the photo diode, the intensity of the laser light can be kept stably for a long period of time, irrespective of a characteristic fluctuation due to an ambient environmental change or aging.

Meanwhile, in case that a gas is measured by the use of the laser light output by the laser light source, the stability of the intensity of the laser light is also important, however, furthermore, it is necessary to make the center oscillation wavelength of the laser light stably coincided with the peak absorption wavelength of the gas. If the oscillation wavelength of the laser light deviates from the peak absorption wavelength of the gas, the intensity of the light of the gas absorption wavelength in the wavelength component of the laser light rapidly decreases because the wavelength band of the laser light is extremely narrow, thereby significantly lowering the analysis accuracy.

Then conventionally, as described in the patent document 1, a part of the laser light is introduced into a cell that contains a gas of the same kind as that of the analysis object gas and the intensity of the light passing the cell is measured so as to verify whether or not the oscillation wavelength of the laser light is kept accurately.

In addition, an infrared spectrophoto analyzer by the use of the laser light source as shown in the patent document 2 stabilizes an optical path by mechanically assembling optical systems with multiple optical elements positioned accurately.
Patent document 1: Japan patent laid open number 2001-21493
Patent document 2: WO95/26497

DISCLOSURE OF THE INVENTION

Problems to be Solved by the Invention

However, with the above-mentioned conventional arrangement, the device becomes bulky and a number of the components increases, thereby becoming disadvantageous in cost-effectiveness. In addition, this arrangement requires accurate positioning of each optical component, becomes weak to vibration and difficult to keep the temperature of each optical component constant so that it becomes sensitive against disturbance (vibration or heat), thereby incurring a drop in a measurement accuracy.

The present claimed invention intends to solve all of the problems and a main object of this invention is to provide an optical analyzer that can promote enhancement of measurement sensitivity, cost reduction, downsizing, structural flexibility and disturbance resistance at once, and a laser device used for the optical analyzer.

Means to Solve the Problems

More specifically, a laser device for analyzer in accordance with this invention described in claim 1, comprises a laser light source that outputs light of a wavelength near an absorption wavelength of an analysis object, a wavelength selection element that receives a part of the light output from the laser light source and that selects and leads out the light having a wavelength substantially equal to the absorption wavelength of the analysis object from among wavelengths of the light, a light detection device that detects intensity of the light led out from the wavelength selection element, a drive electric current control device that increases or decreases the drive electric current of the laser light source near a specified electric current value to output the light of the above-mentioned absorption wavelength by the laser light source so as to set the drive electric current at an electric current value at a time when the intensity of the light detected by the light detection device becomes a peak, and a single substrate that is equipped with the laser light source, the wavelength selection element and the light detection device and that can adjust the temperature at a constant level.

In accordance with this arrangement, since the semiconductor laser, the grating and the light detection device that are susceptible to an influence from the temperature change in analysis can be kept at the constant temperature by means of the substrate, it is possible to restrain a characteristic change (for example, intensity of wavelength fluctuation of the laser light for a laser light source, a fluctuation of the selection wavelength for a wavelength selection element, and a fluctuation of the output electric current value for a light detection device) due to the temperature change at once so that vulnerability against the temperature can be largely improved.

In addition, since it is possible to make the selection wavelength of the light due to the wavelength selection element coincided with the absorption wavelength (for example, the peak wavelength wherein the absorption is the most in the absorption wavelength band and selected in the absorption wavelength band) of the analysis object securely by stabilizing the characteristic as mentioned, it is possible to downsize the laser device for analyzer by mounting each optical component on the single substrate without using a cell like a conventional arrangement.

In addition, since all of the optical components can be loaded on the single substrate, once they are assembled, displacement of the optical components is difficult to occur and the optical components are strong against vibration.

Furthermore, since the driving electric current value of the semiconductor laser is increased or decreased near the predetermined specified electric current value so as to set the driving electric current value at an electric current value when the light intensity detection value detected by the light detection device becomes the peak, namely, the driving electric current value of the semiconductor laser light source is dynamically controlled so that the center wavelength of the laser light coincides with the absorption wavelength of the analysis object, it is possible to make the wavelength of the laser light coincide with the absorption wavelength of the analysis object and keep it stably for a long period with extremely high accuracy irrespective of the change over time of the semiconductor laser.

In addition, if the temperature of the wavelength selection element is changed by changing the temperature of the substrate, the selection wavelength generally changes. Then it is also possible to correct the wavelength of the semiconductor laser by making use of this characteristics.

In order to promote downsizing, it is preferable that the single substrate makes use of a peltier module, and further preferable that a semiconductor laser is used as the laser light source.

In order to decrease a number of the component, it is preferable that the wavelength selection element is arranged at a position to receive leaked light leaked from a reverse side of a major light ejection exit of the laser light source. With this arrangement, since the leaked light is utilized for stabilizing the output, it is possible to improve the efficiency of utilizing the output light to outside at the most.

In case of the light of mid-infrared area generally used for an infrared analysis, since it is difficult to propagate the light by an optical fiber and it requires that the light propagate directly between the optical components, conventionally this arrangement is susceptible to an influence from the temperature or vibration. Conversely, if the presently claimed invention is applied to the light of mid-infrared area, the effect of this invention, namely, the effect of stabilizing the output light be removing a disturbance such as the temperature or the vibration without utilizing any optical fiber becomes extremely remarkable.

In order to prevent unstable oscillation of the semiconductor laser due to a return light from the wavelength selection element, it is preferable that a return light inhibiting device that inhibits the return light returned from the wavelength selection element to the laser light source is arranged on an optical path between the laser light source and the wavelength selection element.

The semiconductor laser includes a quantum cascade laser.

In addition, the optical analyzer in accordance with this invention described in claim 7, is an optical analyzer that measures a concentration or a density of an analysis object based on intensity of light that is ejected from a laser light source and that passes the analysis object.

The optical analyzer is characterized by comprising a fiber-type analyzing part that is so arranged to refract and propagate the light introduced into inside thereof and to introduce the analysis object on a propagation path of the light, a wavelength selection element whose selective wavelength is set in an absorption wavelength band of the analysis object, a measurement light detection device that detects the intensity of the light selected by the fiber-type analyzing part, and a reference light detection device that detects the intensity of the light led out from the wavelength selection element, and is characterized by that an optical fiber connects between the laser light source and the fiber-type analyzing part, between the fiber-type analyzing part and the measurement light detection device, between the laser light source and the wavelength selection element, and between the wavelength selection element and the reference light detection device respectively.

With this arrangement, since whole of the optical path consists of the optical fiber, positioning of each optical component becomes unnecessary, and a cell such as the gas cell to house the analysis object becomes unnecessary and an installation board or a fixing member can be omitted as well, thereby largely promoting downsizing or reducing a cost.

In addition, since it is possible to improve flexibility in the layout so that the fiber-type analyzing part can be placed at an arbitrary place, it becomes extremely easy to measure a risky explosive analysis object by arranging the fiber-type analyzing part distanced from the semiconductor laser or to conduct a measurement in-situ by placing the fiber-type analyzing part inside of a chamber.

Furthermore, since each optical component is connected through the optical fiber, it is difficult to be affected by disturbance (especially, vibration or noise). In addition, since the intensity of the light ejected from the semiconductor laser is monitored by the reference light detection device, it is easy to control and cancel the output fluctuation of the semiconductor laser resulting from the temperature change.

It is especially preferable to use a semiconductor laser that ejects the light of near-infrared area as the laser light source in accordance with this invention. The reason is that the near-infrared light is of a wavelength relatively easy to be transmitted by the optical fiber. In addition, recent development of a semiconductor optical element is remarkable because it is triggered by the development of the optical communication so that a near-infrared semiconductor laser of high output and low cost has been developed. However, a size of the molecular absorption coefficient of the near-infrared light is small such as $1/10$~$1/5$ of that of the mid-infrared light, conventionally used for a gas measurement field, whose molecular absorption coefficient is 2.5 μm~20 μm. Then, the near-infrared light requires the output that is superior in stability and has extremely less noise. With this invention, since it is possible to stabilize the output of the laser light source as mentioned, it becomes possible to use the semiconductor laser that ejects the light of the near-infrared area for the first time.

In order to make it possible to correct the wavelength of the laser light source, it is preferable to further comprise a temperature adjusting mechanism for the laser light source and a temperature adjusting mechanism for the wavelength selection element. This is because the selection wavelength can be changed by adjusting the temperature of the wavelength selection element.

In order to prevent unstable oscillation of the laser light source due to the return light from the wavelength selection element, it is preferable that the reflected light of the wavelength selection element is introduced to the reference light detection device, and an isolator that inhibits the reflected light from returning to the laser light source is arranged along the optical fiber.

As a preferable embodiment of the optical fiber represented is that another optical fiber is bifurcated from the optical fiber connecting the laser light source and the fiber-type analyzing part so as to be connected to the wavelength selection element, and a further different optical fiber is bifurcated from the above-mentioned another optical fiber so as to be connected to the reference light selection element.

If the fiber-type analyzing part is provided with a groove with a bottom or a bore with a bottom that enables to introduce the analysis object into a side peripheral surface of the optical fiber, and the groove with the bottom or the bore with the bottom is so arranged to reach a part of the light propagation area in the optical fiber, it is possible to directly connect the first optical fiber and the second optical fiber with the fiber-type analyzing part without any joint. In addition, it is easy to improve the measurement accuracy by elongating the fiber-type analyzing part.

In order to downsize the optical analyzer with improving the measurement accuracy by elongating an effective length of the fiber-type analyzing part with, for example, a comb or a coiled shape, it is preferable that the fiber-type analyzing part is curved.

In order to make it possible to measure multiple wavelengths, it is preferable to comprise multiple numbers of the laser light sources whose wavelength differs and multiple numbers of the wavelength selection elements that correspond to each of the laser light sources.

Furthermore, the present claimed invention is not limited to the device having the wavelength selection element, and the wavelength selection element may be substituted by other arrangement. With this arrangement, it is possible to obtain the same effect and operation. As a component to substitute the wavelength selection element represented is a reference cell.

Effect of the Invention

In accordance with this invention described in claim 1, since the laser light source, the wavelength selection element and the light detection device that are susceptible to the influence from the temperature change in analysis can be kept at the constant temperature by means of the substrate, it is possible to largely improve vulnerability against the temperature.

In addition, since each optical component is loaded on the single substrate without using a cell, it is possible to downsize the laser device for analyzer, displacement of the optical components is difficult to occur and the optical components are strong against vibration.

Furthermore, since the light intensity detection value detected by the light detection device is monitored and the driving electric current of the laser light source is dynamically controlled so as to make the center wavelength of the laser light coincided with the peak absorption wavelength of the analysis object, it becomes possible to keep the wavelength of the laser light coincided with the absorption wavelength of the analysis object stably with an extremely high accuracy irrespective of the aging of the laser light source.

In accordance with this invention described in claim 7, since whole of the optical path consists of the optical fiber, it is possible to improve flexibility in the layout of each optical component so that a freedom degree of using mode such as conducting a measurement in-situ is improved. In addition, since there is no need of an installation board or a fixing member to mount each optical component accurately, it is possible to largely promote downsizing or reducing a cost.

Furthermore, since each optical component is connected through the optical fiber, it is difficult to be affected by disturbance (especially, vibration or noise). In addition, it becomes possible to keep the output of the laser light source stably by controlling the electric power supplied to the laser light source in order to stability the output of the reference light detection device.

EXPLANATION OF THE CODE

100 . . . laser device for analyzer
1 . . . peltier module
2 . . . laser light (semiconductor laser)
3 . . . wavelength selection element (grading)
5 . . . light detection device
61 . . . drive current control device (current control circuit)
11 . . . substrate
X100 . . . optical analyzer
X1 . . . laser light (semiconductor laser)
X2 . . . fiber-type analyzing part
X21 . . . groove with bottom
X3 . . . measurement light detection device
X4 . . . wavelength selection element (fiber grating)
X5 . . . reference light detection device
X6 . . . isolator
X7 . . . temperature adjusting mechanism for laser light source
X8 . . . temperature adjusting mechanism for wavelength selection element
X91, X92, X93, X94 . . . optical fiber
X4' . . . reference cell

BEST MODES OF EMBODYING THE INVENTION

Next, embodiments of this invention will be explained, however, this invention is not limited to the following embodiments alone.

<First Embodiment>

Figure 1:
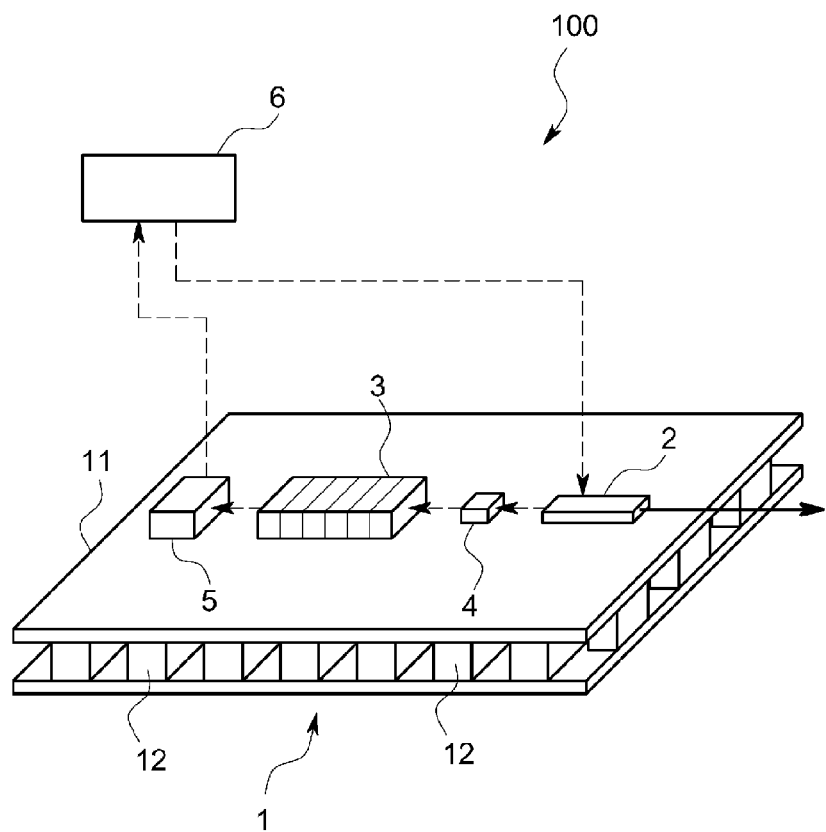
FIG. 1 is a pattern general overall view showing a laser device in a first embodiment of this invention.

A laser device for analyzer 100 in accordance with a first embodiment is used for, for example, an infrared ray gas analyzer that measures a component concentration of an analysis object in a sample gas, and has a structure whose pattern view is shown in FIG. 1.

In FIG. 1, a numerical code 1 indicates a peltier module. The peltier module 1 comprises a plate-shaped single substrate 11, and a peltier element 12 mounted on a back surface of the substrate 11. In this embodiment, the peltier module 1 is further provided with a sensor double with control circuit (not shown in drawings) such as a thermostat for keeping a surface temperature of the substrate 11 constant by operating the peltier element 12.

A numerical code 2 is a semiconductor laser that outputs infrared laser light for analyzing a gas. The semiconductor laser 2 outputs the laser light for analysis in a mid-infrared region (about 2.5 µm~20 µm) from a main exit and ejects the leaked light having substantially the same wavelength of that of the laser light for analysis and intensity of a constant ratio. The semiconductor laser 2 is loaded on the above-mentioned substrate 11. In this embodiment used is the semiconductor laser 2 that outputs the laser light having a center wavelength near an absorption wavelength band of the analysis object at a time when an electric current of a value specified as its specification (hereinafter also called as a specified electric current value) is given.

A reason for using the laser light whose center wavelength is near the absorption wavelength band is that the center wavelength of the output laser light does not necessarily coincide with a peak wavelength in the absorption wavelength band of the analysis object to a substantially acceptable degree for analysis even though the semiconductor laser 2 is driven by the above-mentioned specified electric current value because generally the semiconductor laser has a characteristic that a wavelength slightly fluctuates due to a supplied electric current value or a temperature and has an instrumental error as well.

A numerical code 3 is a transmission-type black grating (hereinafter also called just as a grating) as being a wavelength selection element. A center selective wavelength of the grating 3 substantially coincide with the peak absorption wavelength of the gas as being an analysis object, and the grating 3 is loaded on a propagation path of the leaked light on the substrate 11. In addition, an isolator 4 as being a return light inhibiting device that inhibits a reflected light from the grating 3 from returning to the laser light source is arranged on the propagation path of the leaked light between the grating 3 and the semiconductor laser 2. The isolator 4 is to prevent unstable oscillation of the semiconductor laser 2 due to the reflected light.

A numerical code 5 is a light detection device that detects the intensity of the light derived from the grating 3. The light detection device 5 uses, for example, a photo diode and is loaded on the substrate 11.

Figure 2:
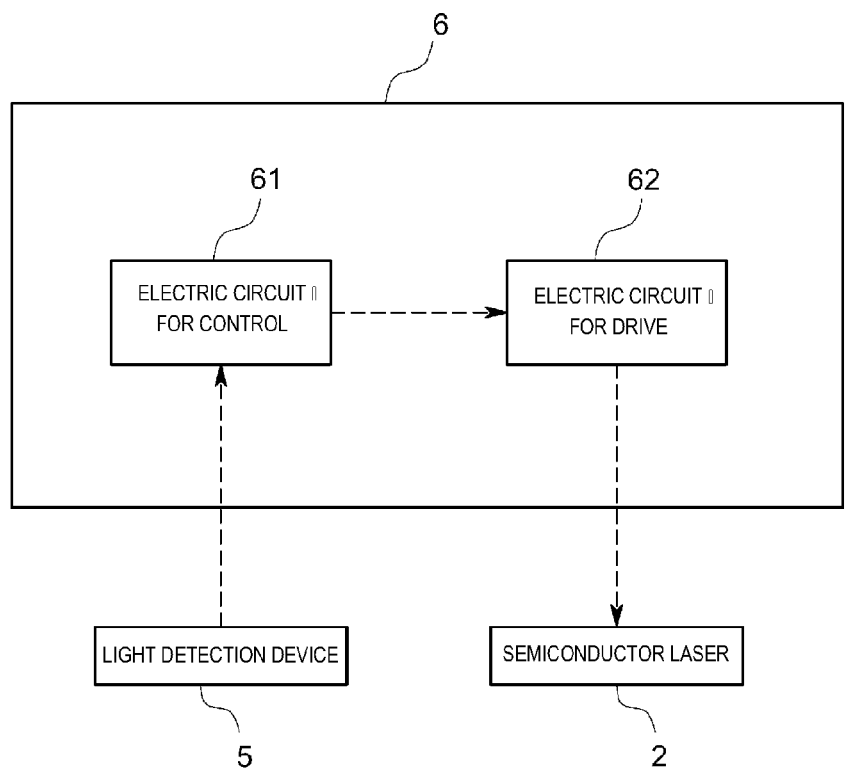
FIG. 2 is a function block diagram of a control device in this embodiment.

A numerical code 6 is a control device that is arranged separately from the peltier module 1 or the semiconductor laser 2 loaded on the peltier module 1 and connected to the peltier module 1 and the semiconductor laser 2 through an electric cable. The control device 6 comprises, as shown in FIG. 2, an electric circuit for control 61 that produces a function as a drive electric current control device and an electric circuit for drive 62 that supplies the semiconductor laser 2 with the electric current.

Next, a behavior of the laser device for analyzer 100 having the above-mentioned arrangement will be explained.

First, a temperature of the substrate 11 is adjusted. The temperature is adjusted by setting a thermostat as mentioned above, however, may be adjusted automatically by making use of the control device 6. Concretely the temperature of the substrate 11 is adjusted by driving the peltier module 1 so that the selective wavelength of the grating 3 stably coincides with the peak absorption wavelength of the analysis object based on the preliminarily measured temperature of the grating 3—the selective wavelength characteristics.

Next, the control device 6 controls the driving electric current value of the semiconductor laser 2 up and down around the specified electric current value so as to search the electric current value where the light intensity value detected by the light detection device 5 becomes the peak and then sets the electric current value at this time as the driving electric current value of the semiconductor laser 2. The reason is that the light intensity detected value indicates the intensity of the laser light passing the grating 3, namely, the intensity of the laser light having the wavelength equal to the absorption wavelength of the analysis object, and the time when the light intensity detected value indicates the peak can be said to be a time when the semiconductor laser 2 outputs the laser light having the center wavelength equal to the peak absorption wavelength of the analysis object.

Figure 3:
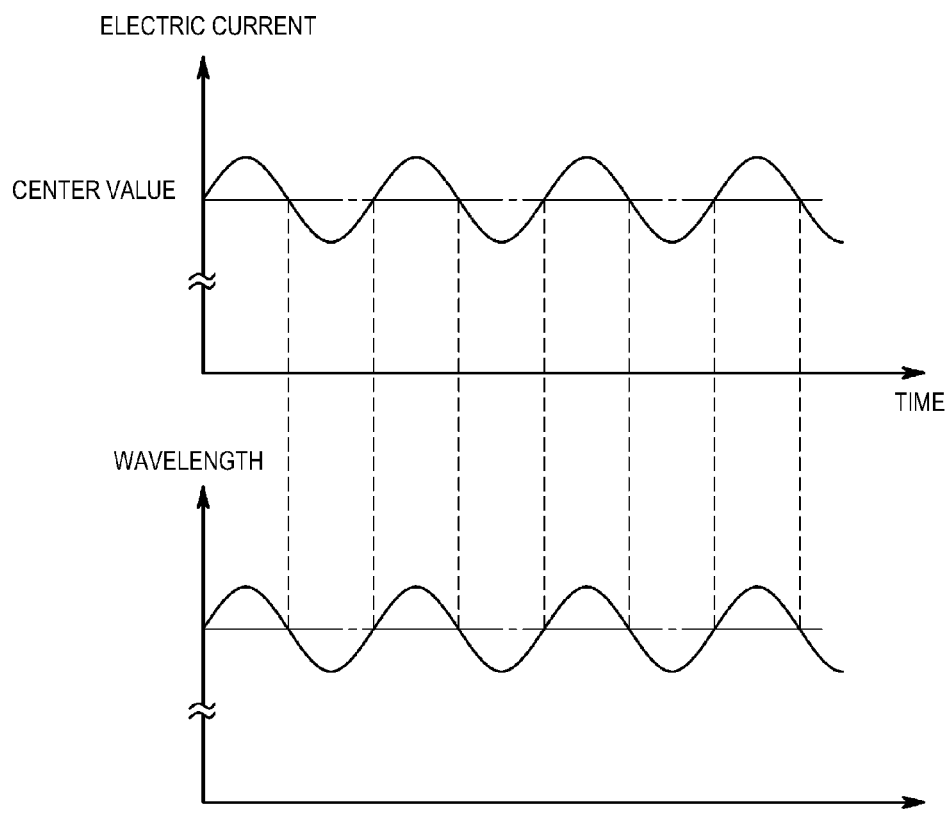
FIG. 3 is an explanatory view to explain a wavelength control principle in this embodiment.

If explaining its searching behavior more concretely, as shown in FIG. 3, the control device 6 gives a sinusoidal electric current having a constant cycle with a constant bias to the semiconductor laser 2. The center value (the bias value) of the sinusoidal electric current in this initial state is set to coincide with the above-mentioned specified electric current value and its vertical movement width is set within a range (for example, within ±20% of the specified electric current value) wherein the intensity of the output laser light does not change drastically.

Since the laser light output from the semiconductor laser 2 fluctuates in accordance with a change of the driving electric current, the wavelength of the laser light oscillates in synchronization with the above-mentioned sinusoidal electric current as shown in FIG. 3.

Next, the control device 6 receives an output signal from the light detection device 5 and measures an interval between peaks of the light intensity detected value shown by the output signal. Then the control device 6 adjusts the center value of the sinusoidal electric current so that the interval becomes constant and sets the center value as the driving electric current value of the semiconductor laser 2.

The reason is as follows.

Figure 4:
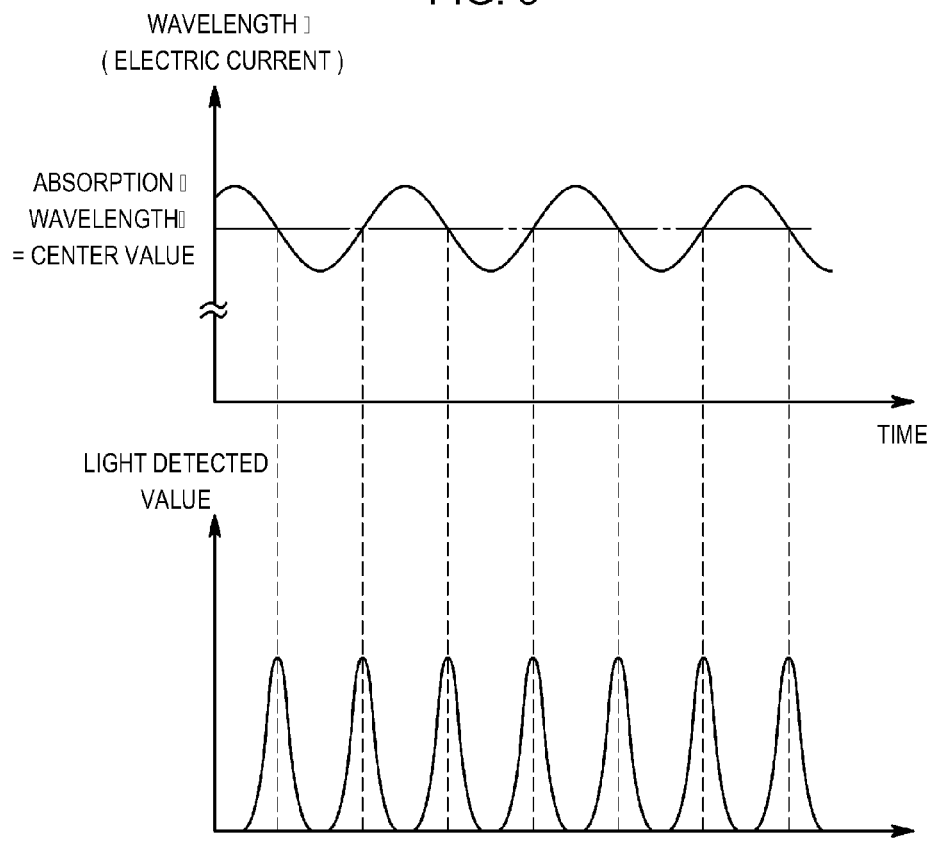
FIG. 4 is an explanatory view to explain the wavelength control principle in this embodiment.

On the occasion that the center wavelength of the laser light output by the semiconductor laser 2 coincides with the peak absorption wavelength of the analysis object at the center value of the above-mentioned sinusoidal electric current, as shown in FIG. 4, only at a time of being driven by the electric current of the above-mentioned center value (including in the vicinity of the center value) the laser light passes the grating 3 and is received by the light detection device 5. As a result, the peak interval of the monitored light intensity detected value is just a half cycle of the oscillation cycle of the above-mentioned sinusoidal electric current and becomes a constant as well.

Figure 5:
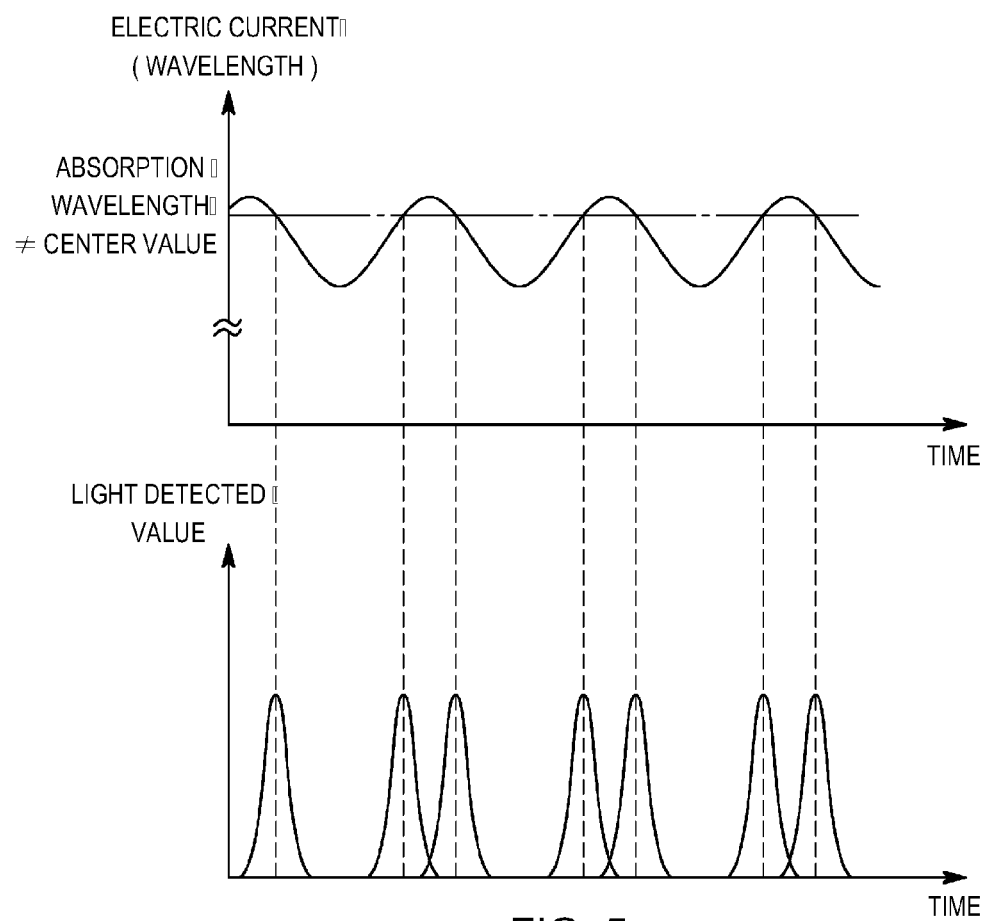
FIG. 5 is an explanatory view to explain the wavelength control principle in this embodiment.

Meanwhile, on the occasion that the center wavelength of the laser light output by the semiconductor laser 2 deviates from the absorption wavelength of the analysis object at the center value of the above-mentioned sinusoidal electric current, as shown in FIG. 5, at a time of being driven by the deviated electric current (including in the vicinity of the deviated current) the laser light passes the grating 3 and is received by the light detection device 5. As a result, a long interval between the peaks of the light intensity detected value and a short interval thereof appear in turn with respect to the input sinusoidal cycle. In addition, in case that the deviance is big, there is a possibility that the light intensity detected value does not appear at all.

As a result, as mentioned above, if the semiconductor laser 2 is driven at the center value of the sinusoidal electric current at a time when the appearance interval of the light intensity detected value is constant, it is possible to accord the center wavelength of the laser light output from the semiconductor laser 2 and the peak absorption wavelength of the analysis object, in other words, to lock up the center wavelength of the laser light at the peak absorption wavelength of the analysis object without deviance.

If a deflection width of the driving electric current value for searching the optimum wavelength is set too big, a fluctuation range of the laser light intensity itself due to increase and decrease of the driving electric current value becomes too big, which will be a cause of a wavelength search error. Then, the initial center value for search is set at the above-mentioned specified electric current value and the vertical movement width (the deflection width) of the sinusoidal current is set as mentioned above as well.

In accordance with the laser device for analyzer 100 of the first embodiment, since the semiconductor laser 2, the grating 3 and the light detection device 5 that are susceptible to an influence from the temperature change in analyzing the gas can be kept at the constant temperature by means of the substrate 11, it is possible to largely improve vulnerability against the temperature.

In addition, since the selective wavelength of the light by the grating 3 can be securely coincided with the absorption wavelength of the analysis object with the temperature stabilized, it is possible to downsize the laser device for analyzer 100 with loading each component on the single substrate 11.

Furthermore, as mentioned, since all of the optical components can be loaded on the single substrate 11, once they are assembled, displacement of the optical components is difficult to occur and the optical components are strong against vibration.

In addition, since the light intensity detected value is monitored by the light detection device 5 and the driving electric current value of the semiconductor laser 2 is dynamically controlled so that the center wavelength of the laser light is locked in the absorption wavelength band (for example, the peak absorption wavelength as mentioned) of the analysis object, it is possible to make the wavelength of the laser light coincide with the absorption wavelength of the analysis object and keep it stably for a long period with extremely high accuracy irrespective of the change over time of the semiconductor laser 2.

<Modified Embodiment>

Next, a modified embodiment of this invention will be explained. The same parts as those in the first embodiment are denoted by the same reference codes as those in the first embodiment.

Figure 6:
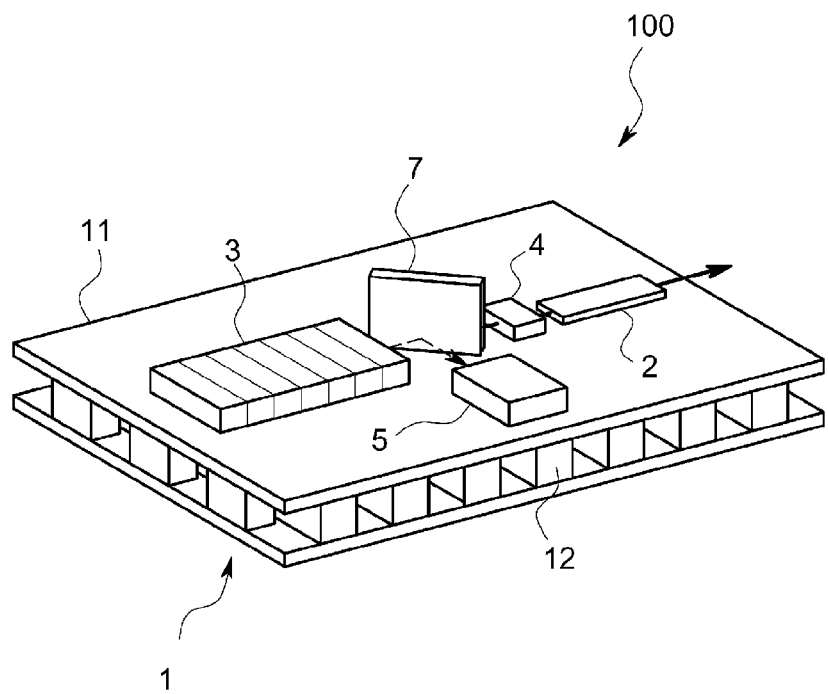
FIG. 6 is a pattern general overall view showing a laser device in a modified example of the first embodiment.

For example, as shown in FIG. 6, a reflective grating 3 may be used and a part of the leaked light reflected from the grating 3 may be introduced into the wavelength selection element 5 by the use of the beam splitter 7 (half mirror).

In addition, the driving electric current of the semiconductor laser 2 for searching the wavelength is the biased sinusoidal electric current in the first embodiment, however, the semiconductor laser may be driven by a DC current. In this case, the electric current supplied to the semiconductor laser is increased or decreased within a certain range of the specified electric current value and an electric current value at a time when the peak (an inflexion point) appears in the light detected value within the certain range may be set as the driving electric current value of the semiconductor laser.

Furthermore, a quantum cascade laser (QCL) or other may be used as the laser light source, and a multilayer interference filter, a photonic crystal, an etalon, a gas cell may be utilized for the wavelength selection element.

In addition, it is a matter of course that other than the peltier module may be utilized for the temperature adjusting device. In stead of the isolator, a plate-shaped light reflecting element having an extremely small laser light passing bore such as a pin hole may be arranged with inclined to the laser optical path as the return light inhibiting device.

>Second Embodiment>

Next, a second embodiment will be explained. In the second embodiment, reference codes in this embodiment are irrelevant to the reference codes in the first embodiment.

Figure 7:
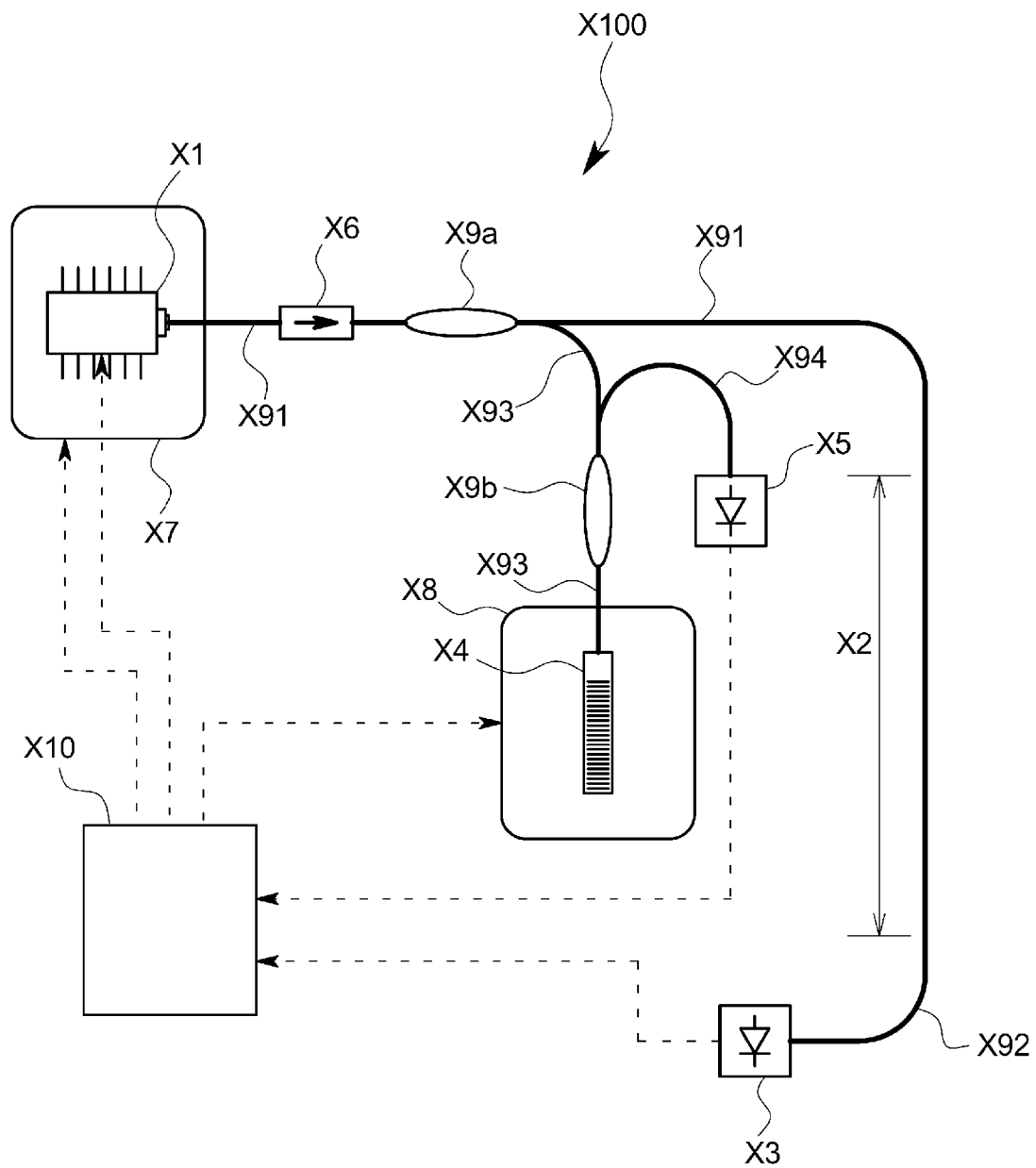
FIG. 7 is a pattern overall view showing an overall of an optical analyzer in a second embodiment of this invention.

An optical analyzer X100 in accordance with this second embodiment is an infrared gas analyzer to detect a concentration of, for example, a water vapor ($H_2O$) contained in a sample gas, and has an arrangement whose pattern diagram is shown in FIG. 7

In FIG. 7, a reference code X1 is a semiconductor laser that ejects the infrared light as being a measurement light for analyzing the gas. The semiconductor laser X1 uses a coherent light of near-infrared area (about 0.8 μm~about 2.5 μm, for example 1390 nm in order to measure a concentration of $H_2O$ in this embodiment).

Figure 8:
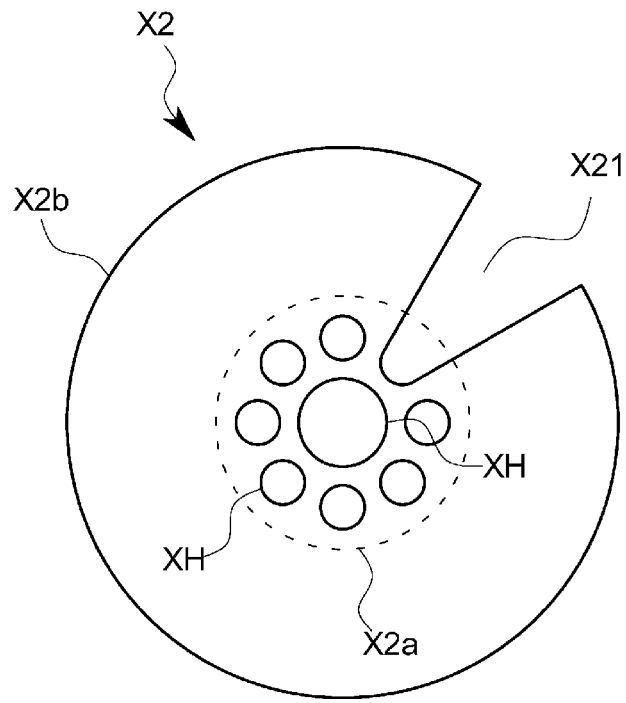
FIG. 8 is a cross sectional end view showing a fiber type analyzing part in this embodiment.
Figure 9:
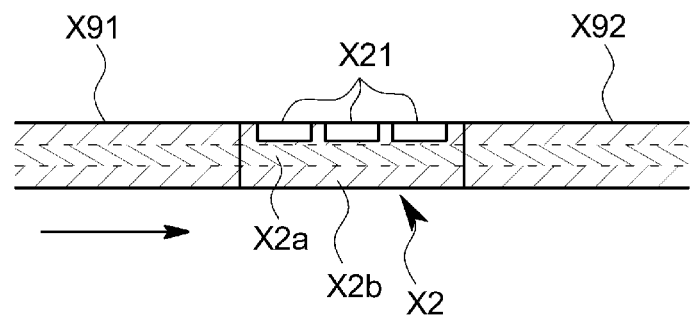
FIG. 9 is a longitudinal sectional view showing the fiber type analyzing part in this embodiment.

A reference code X2 is a fiber-type analyzing part exposed in the sample gas. The fiber-type analyzing part X2 comprises, as shown in FIG. 8 and FIG. 9, a core X2a and a clad X2b, and refracts and propagates the light in the boundary area between the core X2a and the clad X2b similar to the optical fiber, and one end of the fiber-type analyzing part X2 is connected to the semiconductor laser X1 through a first optical fiber X91. The core X2a is, as shown in FIG. 8, formed, for example, by arranging multiple thin bores XH extending in the axial direction at a center part of the fiber-type analyzing part X2. On a side peripheral surface of the fiber-type analyzing part X2, a groove X21 with a bottom that reaches both the core X2a and the light propagation area formed at the periphery of the core X2a is bored to extend in the axial direction. When the sample gas is introduced into the groove X21, the light propagating inside of the fiber-type analyzing part X2 is attenuated by the water vapor as being the analysis object in the gas so as to lessen the intensity of the light that passes inside of the fiber-type analyzing part X2 and that is output from the other end thereof.

A reference code X3 is a measurement light detection device. The measurement light detection device X3 uses, for example, a photo diode and is connected to the other end of the fiber-type analyzing part X2 through a second optical fiber X92.

As mentioned, since the fiber-type analyzing part X2 is made of the optical fiber having the groove X21 and has the same diameter as that of each of the first and the second optical fibers X91, X92, the fiber-type analyzing part X2 is connected to the first optical fiber X91 and the second optical fiber X92 by means of fusion. The fiber-type analyzing part X2 may be connected to the first and the second optical fibers X91, X92 by the use of a connector.

A reference code X4 is a reflective fiber grating as being the wavelength selection element so as to set the selective wavelength band coincides with the absorption wavelength of the $H_2O$ gas as being the analysis object. The reflective fiber grating X4 is connected to a distal end of a third optical fiber X93 bifurcated from the first optical fiber X91 by the use of a coupler X9a, and receives a part (about ⅒, in this case) of the light from the semiconductor laser X1 through the first optical fiber X91 and the third optical fiber X93 and reflects only the light whose wavelength coincides with the absorption wavelength of the $H_2O$ gas and returns it to the third optical fiber X93.

A reference code X5 is a reference light detection device that detects the intensity of the light selected by the fiber grating X4. The reference light detection device X5 uses, for example, a photo diode similar to the measurement light detection device X3, and is connected to a distal end of a forth optical fiber X94 bifurcated from the third optical fiber X93 by the use of a coupler X9b.

A reference code X6 is an isolator that isolates the reflected light from the fiber grating X4 from returning to the laser light source, and is arranged between the coupler X9a of the first optical fiber X91 and the semiconductor laser X1. The isolator X6 prevents unstable oscillation of the semiconductor laser X1 due to the reflected light.

A reference code X7 is a temperature adjusting mechanism for laser light source to keep the temperature of the semiconductor laser X1 constant and to stabilize an output of the semiconductor laser X1. The temperature adjusting mechanism for laser light source X7 comprises, a peltier module inside of which, for example, a peltier element is provided, and a thermostat (not shown in drawings) to keep the temperature of the surface substrate of the peltier module by operating the peltier element and a control circuit (not shown in drawings), and the semiconductor laser X1 is loaded on the surface substrate.

A reference code X8 is a temperature adjusting mechanism for wavelength selection element to keep the temperature of the fiber grating X4 constant and to stabilize its characteristics. The temperature adjusting mechanism for wavelength selection element X8 can adjust the temperature independently from the temperature adjusting mechanism for laser light source X7 and comprises a peltier module and its peripheral devices to control the peltier module similar to the temperature adjusting mechanism for laser light source X7. The fiber grating X4 is loaded on the surface substrate of the peltier module.

A reference code X10 is an information processing unit that receives an output signal from each of the light detection devices X3, X5, and controls the electric current supplied to the semiconductor laser X1 and each temperature adjusting mechanism X7, X8 and calculates a concentration of the $H_2O$ gas as being the analysis object. The information processing unit X10 makes use of, for example, an analog circuit, or a digital circuit such as a CPU.

Next, an operation of the optical analyzer X100 will be explained.

First, a controlling operation and initial setting by the information processing unit X10 will be explained.

The light ejected from the semiconductor laser X1 is introduced into the first optical fiber X91, and a certain ratio of the introduced light is introduced into the fiber grating X4 through the third optical fiber X93. Then only the light of the absorption band wavelength of the $H_2O$ is reflected by the fiber grating X4 and introduced into the reference light detection device X5 through the forth optical fiber X94.

Since the reference signal output by the reference light detection device X5 indicates the intensity of the light of the absorption wavelength band of the gas component output by the semiconductor laser X1, the information processing unit X10 or an operator adjusts the temperature of the semiconductor laser X1 by operating the temperature adjusting mechanism for laser light source X7 so that a value of the reference signal becomes the maximum, namely, the output wavelength of the semiconductor laser X1 coincides with the absorption wavelength band of the sample gas. The value of the reference signal at this time is stored as a target value by the information processing unit X10 and then the information processing unit X10 controls an electric current supplied to the semiconductor laser X1 at the target value so as to stabilize the output of the electric current in order to eliminate an influence due to deterioration of the semiconductor laser X1.

Next, the sample gas whose concentration is known is introduced into the cell and the output from the measurement light detection device X3 is measured and then corrected. The corrected data is stored in the information processing unit X10. Correction is conducted regularly in order to eliminate the influence on the fiber-type analyzing part due to contamination by the gas.

Measurement is started after completion of the initial setting.

Since the light from the semiconductor laser X1 passes the fiber-type analyzing part X2 and is irradiated on the measurement light detection device X3, when the gas is introduced into the fiber-type analyzing part X2, the measurement signal output from the measurement light detection device X3 indicates the intensity of the light after the light is output from the semiconductor laser X1 and absorbed into the gas.

As a result, the information processing unit X10 receives the measurement signal and calculates the concentration of the gas component as being the analysis object based on the value of the measurement signal and the previously memorized correction data.

In accordance with this arrangement, since whole of the optical path from the semiconductor laser X1 as being the light source to the light detection device consists of the optical fiber, positioning of each optical component (the semiconductor laser X1, the fiber-type analyzing part X2, the grating X4 or the like) becomes unnecessary, and a cell such as the gas cell to house the analysis object becomes unnecessary and an installation board or a fixing member can be omitted as well, thereby largely promoting downsizing or reducing a cost.

In addition, since it is possible to improve flexibility in the layout so that the fiber-type analyzing part X2 can be placed at an arbitrary place, it becomes extremely easy to measure a risky explosive analysis object by arranging the fiber-type analyzing part X2 distanced from the semiconductor laser X1 or to conduct a measurement in-situ by placing the fiber-type analyzing part X2 inside of a chamber.

Furthermore, since each optical component is connected through the optical fiber X91, X92, X93, X94, it is difficult to be affected by disturbance (especially, vibration or noise). In addition, since the intensity of the light ejected from the semiconductor laser X1 is monitored by the reference light detection device X5, it is easy to control and cancel the output fluctuation of the semiconductor laser X1 resulting from the temperature change.

With this arrangement, since the near-infrared semiconductor laser X1 that is of high output and inexpensive can be used for analyzing the gas for the first time, it is possible to further promote low-cost largely also on this point.

<Modified Form>

Next, a modified form of the second embodiment will be explained. In the following explanation and drawings, the same parts as those in the second embodiment are denoted by the same reference codes as those in the second embodiment.

Figure 10:
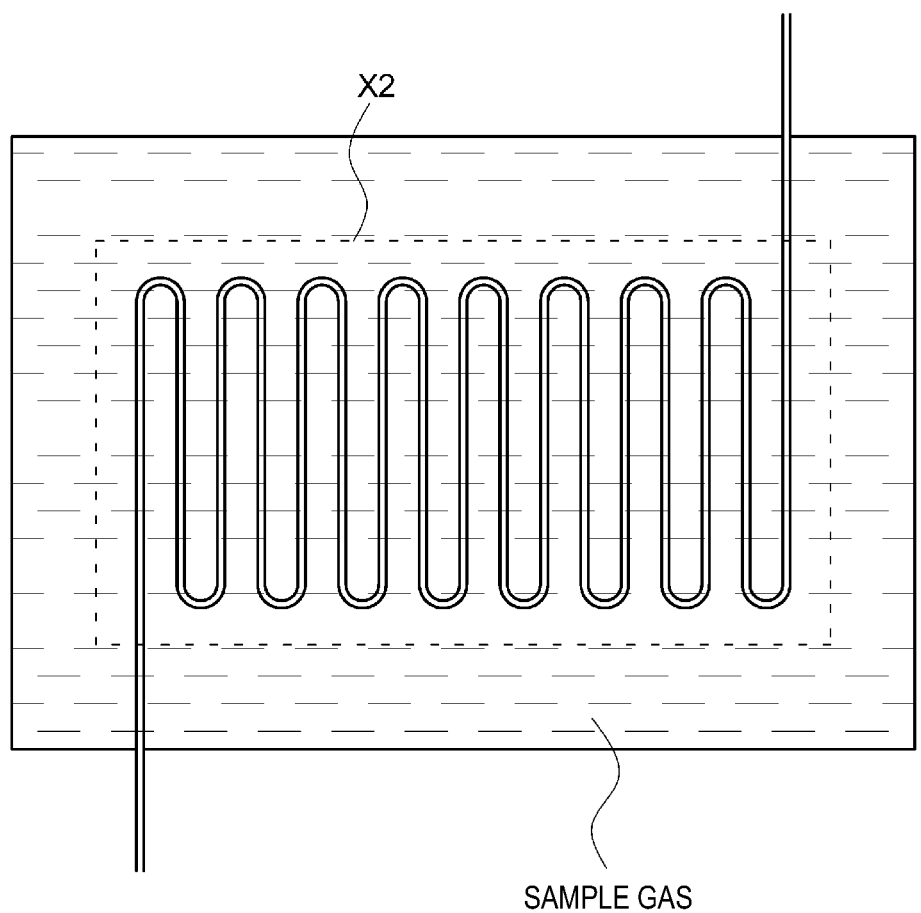
FIG. 10 is a general view showing a fiber type analyzing part in a modified example of the second embodiment.

A shape of the fiber-type analyzing part X2 is not limited to a straight line like the above-mentioned second embodiment, and the fiber-type analyzing part X2 may be, for example, comb-shaped by curving the optical fiber multiple times as shown in FIG. 10 or shaped in a coil so that a contact area with the sample gas is increased while the compactness is kept so as to improve an analysis sensitivity. Ordinarily, it is unthinkable to tightly curve the optical fiber as shown in FIG. 10 in a communication field because it reduces a light transmission efficiency, however, since an object of this arrangement is not to transmit the light efficiency but to monitor an absorption degree by the gas, there is no problem in curving the optical fiber.

Figure 11:
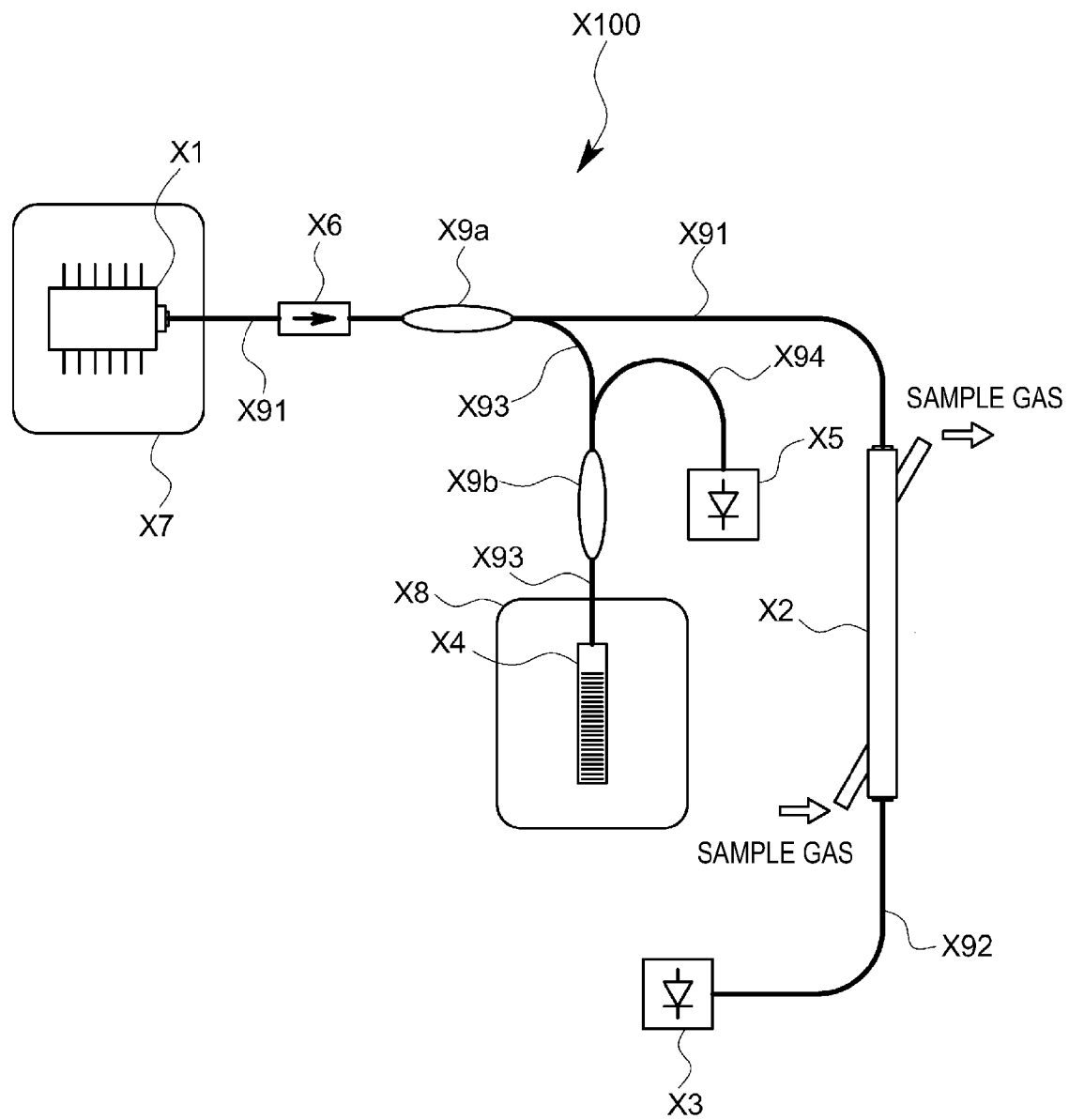
FIG. 11 is a pattern overall view showing an optical analyzer in other modified embodiment.

In addition, it is conceivable to use a hollow fiber as shown in FIG. 11 as the fiber-type analyzing part X2. In FIG. 11 adopted is a flow measurement method wherein the sample gas is introduced from one end part side surface and derived from the other end part side surface.

Since the fiber grating has a characteristic that the selective wavelength fluctuates when the temperature of the fiber grating is changed, the wavelength of the semiconductor laser (the laser light source) may be corrected by changing the temperature of the grating with actively utilizing this characteristic.

Figure 12:
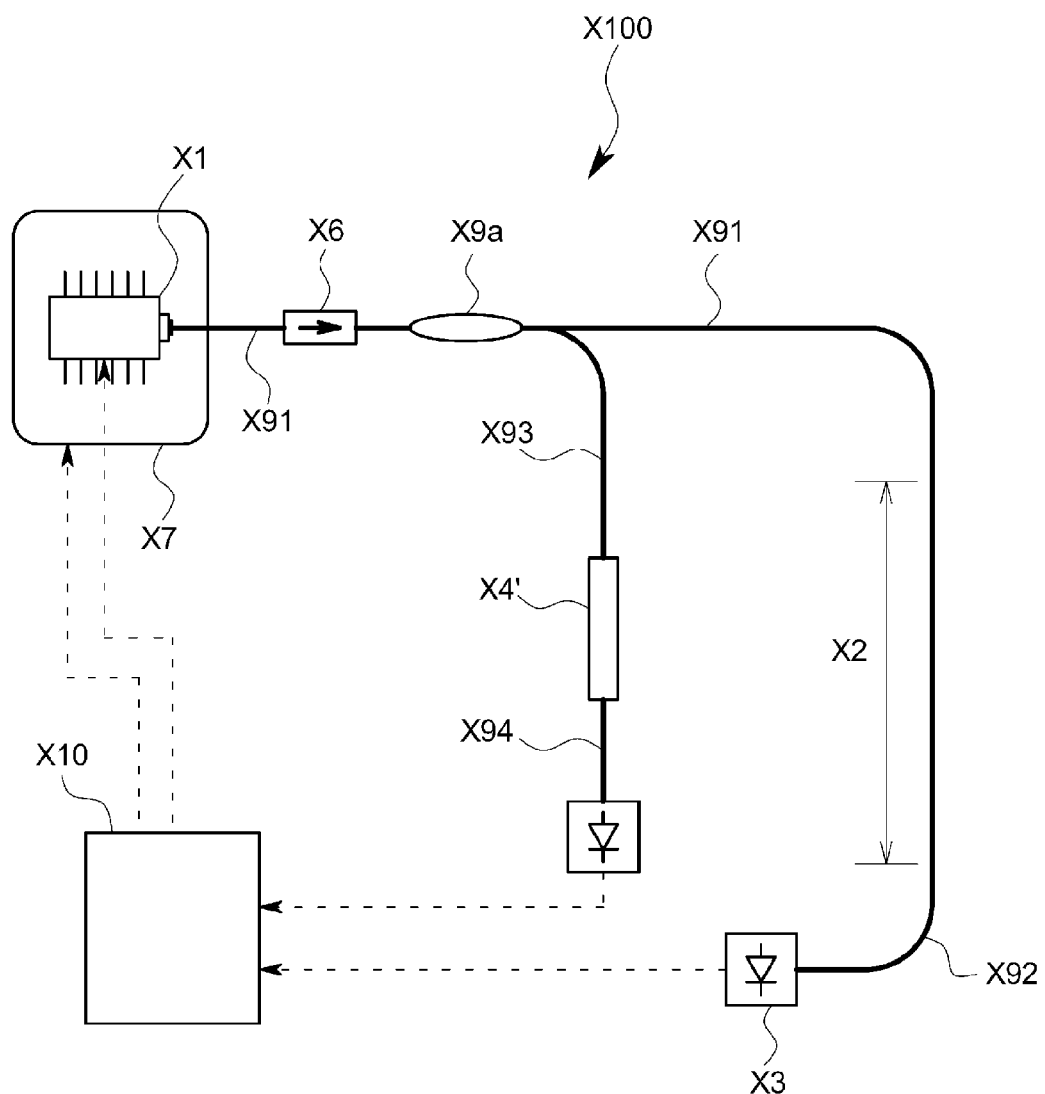
FIG. 12 is a pattern overall view showing an overall of an optical analyzer in a further different modified embodiment.

In addition, from the standpoint of the facility of connection, it is preferable that the wavelength selection element is the fiber grating, however, it may be other diffraction grating or a prism. In stead of the wavelength selection element, a reference cell X4' that holds the gas having substantially the same (or having substantially the same optical characteristics) predetermined concentration as that of the analysis object gas may be utilized as shown in FIG. 12. In this case, the wavelength of the semiconductor laser X1 is adjusted by the laser light source temperature adjusting mechanism X7 so as to minimize the output of the reference light detection device X5, namely, to strengthen the absorption the most. With this arrangement, the wavelength of the semiconductor laser X1 can be fixed to the absorption wavelength of the analysis object gas.

Figure 17:
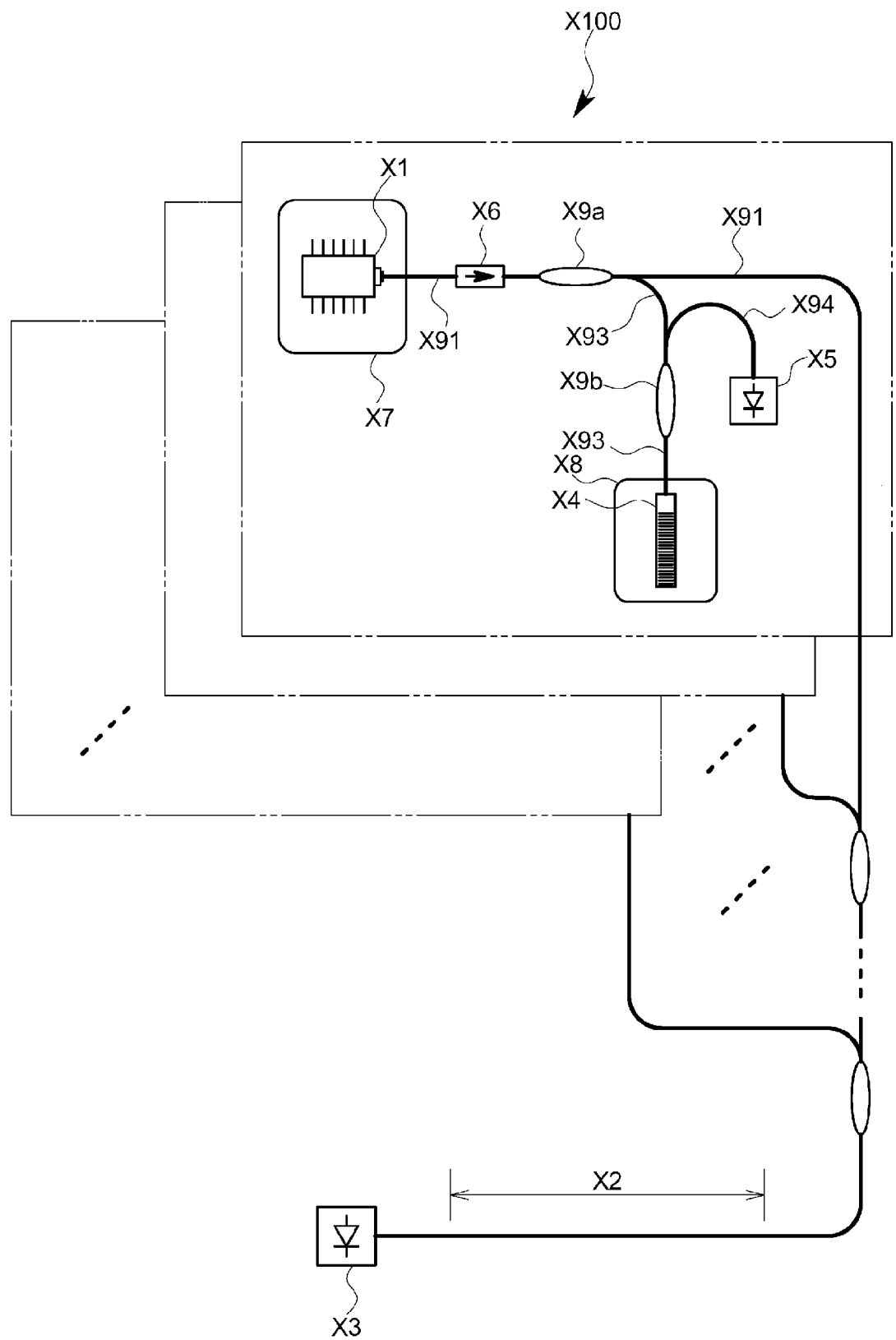
FIG. 17 is a pattern overall view showing an overall of an optical analyzer in the further different modified embodiment.
Figure 18:
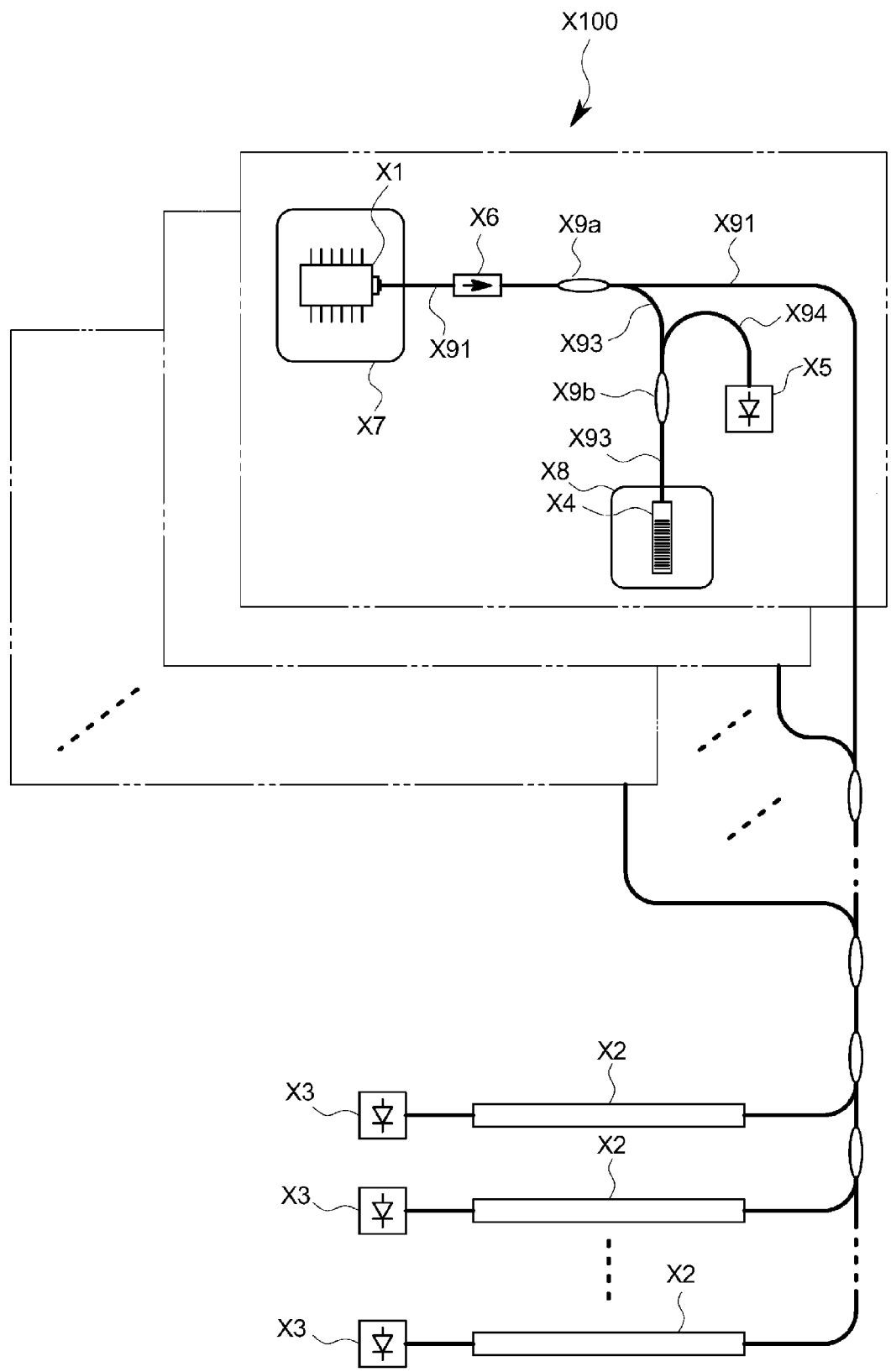
FIG. 18 is a pattern overall view showing an overall of an optical analyzer in the further different modified embodiment.

In addition, as shown in FIG. 17, an arrangement can be conceived that multiple pairs each of which comprises the laser light source X1 of a different wavelength and the wavelength selection element X4 are connected to a single fiber-type analyzing part X2 in parallel so as to enable the measurement of multiple wavelengths. In this case, for example, each laser light source may be so arranged to emit the light at a different time (time-sharing emission). Furthermore, as shown in FIG. 18, the same number of the fiber-type analyzing parts X2 and the measurement light detection devices X3 as that of the laser light source X1 may be arranged in parallel. With this arrangement, it is possible to conduct the measurement by making each light source X1 emit the light simultaneously.

Multiple filters each of which passes the light having a different wavelength may be arranged in a measurement light detection device side and each laser light source emits the light simultaneously (in this case, not only the laser light source but also a white light source may be used) so that multiple wavelengths can be measured by switching the filter in a time-sharing manner.

Figure 19:
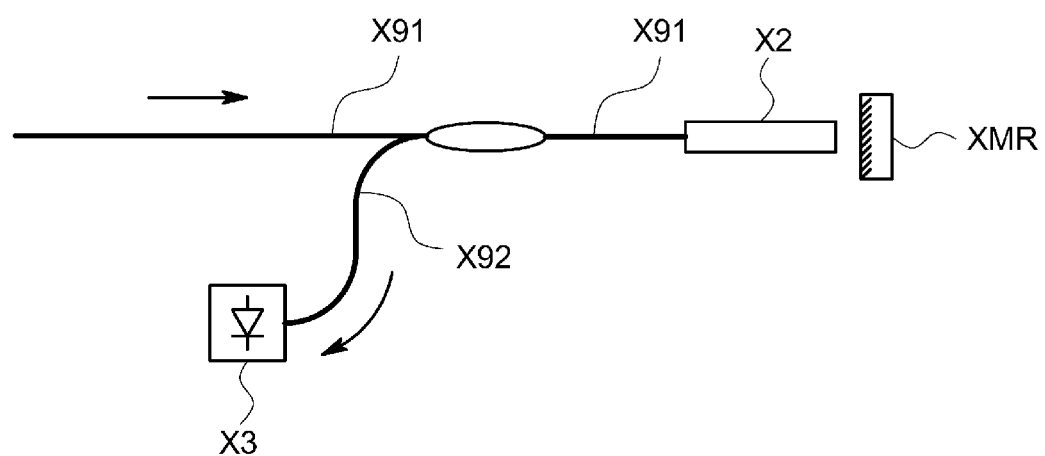
FIG. 19 is a pattern overall view showing a part of an optical analyzer in the further different modified embodiment.

Furthermore, as shown in FIG. 19, a reflecting mirror XMR may be arranged at an output end of the fiber-type analyzing part X2 so that the light output through the fiber-type analyzing part X2 is propagated in a reversed direction of the input light to an optical fiber X91 (equivalent to the above-mentioned first optical fiber X91) for input to the fiber-type analyzing part X2. In this case, a coupler for bifurcation is arranged in the way of the optical fiber X91 for input so that only the light returned through the fiber-type analyzing part X2 is bifurcated by the coupler for bifurcation and introduced to an optical fiber X92 (equivalent to the above-mentioned second optical fiber X92) for output so that the measurement light detection device X3 arranged at a distal end of the optical fiber X92 detects the intensity of the return light.

In addition, a mode of the analyzing part is not limited to the fiber-type, and may be an ordinary gas cell or the like. Also with this arrangement, since it is possible to separate the analyzing part alone from the laser light source, the measurement light detection device, or other optical member such as the wavelength selection element through the optical fiber in, for example, a unit of km, it is possible to secure safety in dealing with a risky gas such as an explosive gas or a toxic gas.

The optical analyzer in accordance with this invention can be applied to a liquid other than the gas or other physical or chemical phenomenon.

Figure 13:
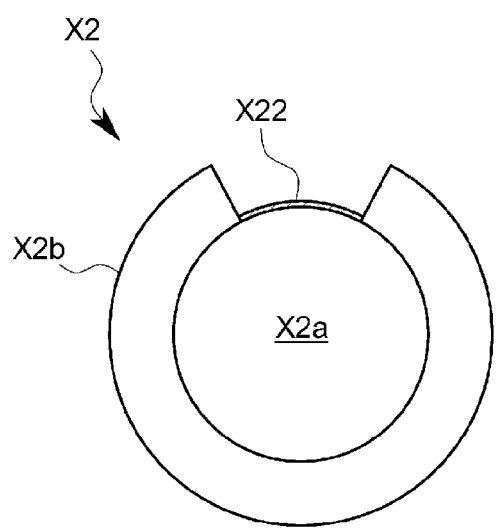
FIG. 13 is a cross sectional end view showing a fiber type analyzing part in a further different modified embodiment.
Figure 14:
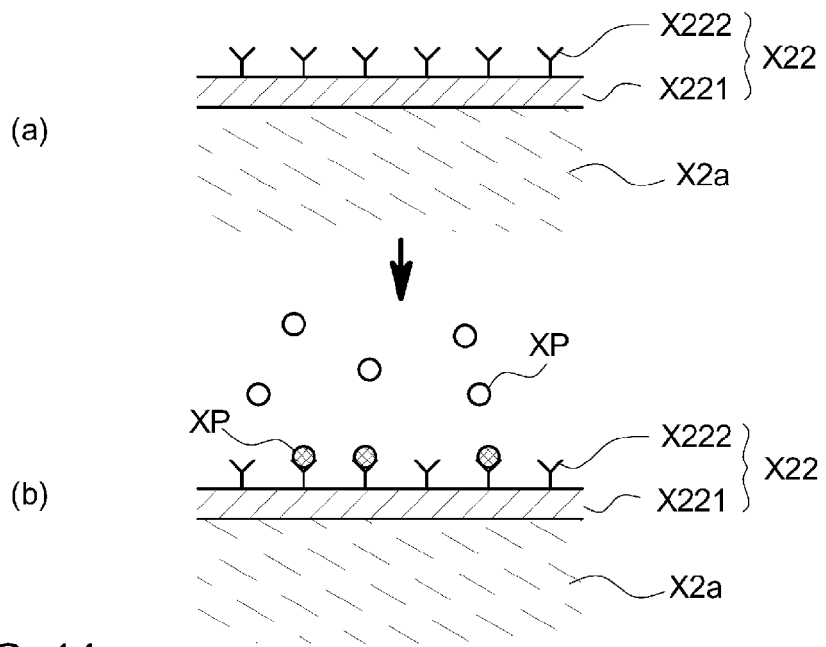
FIG. 14 is a pattern partial enlarged view to explain a capture member and its operation in this modified embodiment.

For example, in case that a protein is the analysis object, this optical analyzer can be applied to a protein sensor. FIG. 13 shows a cross-sectional view of the fiber-type analyzing part X2 of this case. The fiber-type analyzing part X2 has such an arrangement that a surface of a core X2a exposed by cutting a part of a clad X2b of the optical fiber is covered by a capture member X22 that captures the analysis object. As shown in FIG. 14(a) wherein a magnified part of the capture member X22 is shown, the capture member X22 comprises an Au film X221 that coats an exposed part of the core X2a, and an antigen or an antibody X222 immobilized on a surface of the Au film X221. The antigen or the antibody X222 causes antigen/antibody reactivity with the protein XP to be sensed and unites them (refer to FIG. 14(b)). In addition, a divergence angle of the light from the second optical fiber X92 is measured by the use of, for example, a surface sensor as the measurement light detection device.

Figure 15:
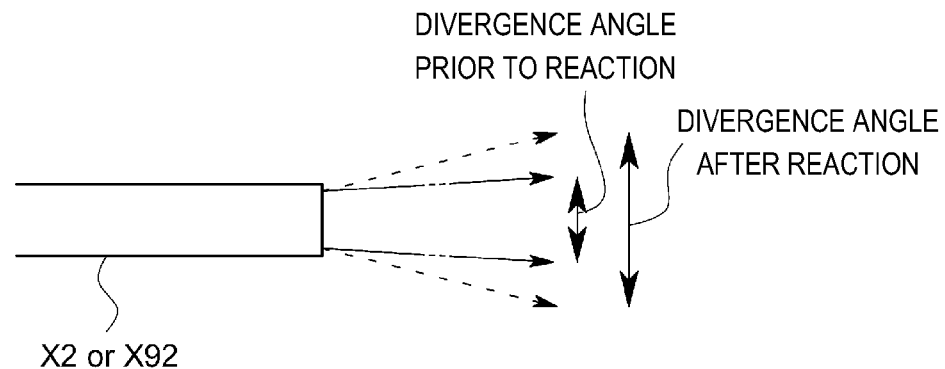
FIG. 15 is an explanatory view showing a diffusing angle in this modified embodiment.
Figure 16:
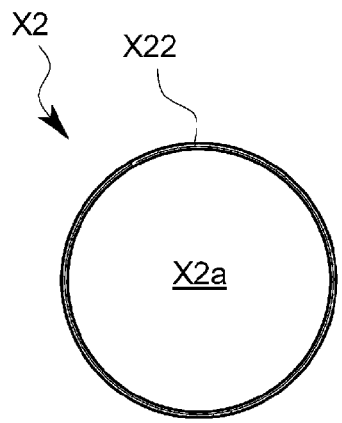
FIG. 16 is a cross sectional end view showing a fiber type analyzing part in the further different modified embodiment.

In accordance with this arrangement, as shown in FIG. 14(b), at a time when the protein XP as being the analysis object is captured by the capture member X22 since the divergence angle of the light coming from the fiber-type analyzing part X2 (or the second optical fiber X92 connected to the fiber-type analyzing part X2) becomes bigger than the divergence angle of the light prior to the capture as shown in FIG. 15, it is possible to detect the concentration of the protein by reading out the change of the divergence angle.

In addition, all of the clad X2b may be removed so as to be the core X2a alone as shown in FIG. 15, and the capture member covers the surface of the core X2a. With this arrangement, it is possible to conduce a measurement with higher accuracy.

With the same arrangement, it is also possible to detect the hybridization reactivity of DNA. In the above embodiment, the antigen is immobilized on the surface of Au, however if a probe DNA is immobilized instead of the antigen, it is possible to detect the target DNA.

With an arrangement of covering the core with titanium oxide, it is possible to perform a function as an organic matter detection sensor. When photo-oxidation energy is given to titanium oxide, the energy is attenuated and the wavelength of the light introduced into the fiber-type analyzing part changes. If there are a lot of organic matters in the sample, the light energy is consumed by an amount of the photo-oxidation and attenuated due to the photo-oxidation so that the wavelength changes. In addition, the photo-oxidation action of titanium oxide changes due to an amount of oxygen. As a result, it is also possible to use this device as an oxygen concentration sensor. In accordance with this device, since the optical analyzer can be downsized as small as, for example, a conveniently portable size, it is also possible to mount this device on a cellular phone.

In addition, it is possible to apply the optical analyzer to a humidity sensor, an $H_2O$ sensor, an $NO_x$ sensor incorporated into a traffic light, an NO sensor, a blood sensor for checkup on the spot (glucose, uric acid), a glucose sensor during operation, a freshness check sensor for food such as a lunch box.

The present claimed invention is not limited to the above-mentioned each embodiment, and may be variously modified by appropriately combining a part of the above-mentioned embodiment without departing from the spirit of the invention.

The invention claimed is:

1. A laser device for analyzer comprising:
   a laser light source configured to output light having a wavelength near an absorption wavelength of an analysis object;

a wavelength selection element configured to receive a part of the light output from the laser light source and configured to select and lead out the light having a wavelength substantially equal to the absorption wavelength of the analysis object from among wavelengths of the light;

a light detection device configured to detect intensity of the light led out from the wavelength selection element;

a single substrate equipped with the laser light source, the wavelength selection element and the light detection device;

a temperature adjustment mechanism configured to adjust a temperature of the single substrate to a predetermined temperature;

a temperature detector configured to detect whether the temperature of the single substrate is kept at the predetermined temperature; and a drive electric current control device configured to control a drive electric current of the laser light source and including a drive electric current oscillator configured to, in a state that the temperature detector detects that the temperature of the single substrate is kept at the predetermined temperature, oscillate the drive electric current of the laser light source near a specified electric current value to output the light at the absorption wavelength of the analysis object, a searching part configured to search an electric current value at a time when the intensity of the light detected by the light detection device becomes a peak while the drive electric current oscillator oscillates the drive electric current of the laser light source, and a setting part configured to stop the oscillation of the drive electric current of the laser light source and set the drive electric current at the electric current value that is searched by the searching part.

2. The laser device for analyzer described in claim 1, wherein the temperature adjustment mechanism includes a peltier module.

3. The laser device for analyzer described in claim 1, wherein the laser light source is a semiconductor laser.

4. The laser device for analyzer described in claim 1, wherein the wavelength selection element is arranged at a position to receive leaked light leaked from a reverse side of a major light ejection exit of the laser light source.

5. The laser device for analyzer described in claim 1, wherein the laser light source ejects the light of mid-infrared area.

6. The laser device for analyzer described in claim 1, wherein a return light inhibiting device that inhibits return light returned from the wavelength selection element to the laser light source is arranged on an optical path between the laser light source and the wavelength selection element.

7. A gas analyzer comprising:

a laser light source configured to output light having a wavelength near an absorption wavelength of an analysis object;

a wavelength selection element configured to receive a part of the light output from the laser light source and configured to select and lead out the light having a wavelength substantially equal to the absorption wavelength of the analysis object from among wavelengths of the light;

a light detection device configured to detect intensity of the light led out from the wavelength selection element;

a single substrate equipped with the laser light source, the wavelength selection element and the light detection device;

a temperature adjustment mechanism configured to adjust a temperature of the single substrate to a predetermined temperature;

a temperature detector configured to detect whether the temperature of the single substrate is kept at the predetermined temperature; and a drive electric current control device configured to control a drive electric current of the laser light source and including a drive electric current oscillator configured to, in a state that the temperature detector detects that the temperature of the single substrate is kept at the predetermined temperature, oscillate the drive electric current of the laser light source near a specified electric current value to output the light at the absorption wavelength of the analysis object, a searching part configured to search an electric current value at a time when the intensity of the light detected by the light detection device becomes a peak, and a setting part configured to stop the oscillation of the drive electric current of the laser light source and set the drive electric current at the electric current value that is searched by the searching part.

* * * * *